(12) United States Patent
Findlay et al.

(10) Patent No.: US 7,347,840 B2
(45) Date of Patent: Mar. 25, 2008

(54) PATCH FOR LOCATING A TARGET ZONE FOR PENETRATION

(75) Inventors: Judith M. Findlay, Richmond (CA); David L. Johnson, Burnaby (CA); Misha Krasnich, Richmond (CA); Michael W. Jacobs, Surrey (CA)

(73) Assignee: Pyng Medical Corp., Vancouver (CA)

( * ) Notice: Subject to any disclaimer, the term of this patent is extended or adjusted under 35 U.S.C. 154(b) by 110 days.

(21) Appl. No.: 10/860,046

(22) Filed: Jun. 4, 2004

(65) Prior Publication Data

US 2004/0220497 A1    Nov. 4, 2004

Related U.S. Application Data

(62) Division of application No. 09/423,855, filed on Mar. 2, 2000, now Pat. No. 6,761,726.

(51) Int. Cl.
*A61M 5/00*    (2006.01)

(52) U.S. Cl. .............. 604/187; 604/180; 604/181; 604/182; 604/327

(58) Field of Classification Search .......... 604/264, 604/506, 272, 136, 48, 180, 19; 606/80; 128/898
See application file for complete search history.

(56) References Cited

U.S. PATENT DOCUMENTS

| | | | |
|---|---|---|---|
| 2,448,708 A | 9/1948 | Geissler | |
| 3,791,386 A | 2/1974 | McDonald | |
| 3,815,605 A | 6/1974 | Schmidt et al. | |
| 3,991,765 A * | 11/1976 | Cohen | 128/207.29 |
| 4,646,731 A * | 3/1987 | Brower | 606/215 |
| 4,659,329 A * | 4/1987 | Annis | 604/180 |
| 4,711,636 A * | 12/1987 | Bierman | 604/180 |
| 4,874,380 A | 10/1989 | Hesketh | |
| 4,969,870 A | 11/1990 | Kramer et al. | |
| 4,985,019 A | 1/1991 | Michelson | |
| 5,116,324 A * | 5/1992 | Brierley et al. | 604/180 |
| 5,364,361 A | 11/1994 | Battenfield | |
| 5,520,650 A | 5/1996 | Zadini et al. | |
| 5,591,188 A | 1/1997 | Waisman | |
| 5,817,052 A | 10/1998 | Johnson et al. | |
| 5,858,005 A * | 1/1999 | Kriesel | 604/180 |
| 5,868,711 A * | 2/1999 | Kramer et al. | 604/136 |
| 5,891,085 A | 4/1999 | Lilley et al. | |
| 6,017,348 A | 1/2000 | Hart et al. | |
| 6,248,110 B1 | 6/2001 | Reiley et al. | |
| 6,761,726 B1 | 7/2004 | Findlay et al. | |

FOREIGN PATENT DOCUMENTS

CA    2205623    11/1998

* cited by examiner

*Primary Examiner*—Kevin C. Sirmons
*Assistant Examiner*—Phillip Gray
(74) *Attorney, Agent, or Firm*—Pequignot + Myers LLC

(57) ABSTRACT

The present invention relates to a method and apparatus for locating a site of intraosseous infusion and for relieving strain and stress on the infusion site. The template patch uses a key anatomical feature of the bone as a reference point to a target zone for infusion that is located a predetermined distance away from the feature. The template patch has a tube clamp and a covering that protect the infusion site from external forces.

24 Claims, 10 Drawing Sheets

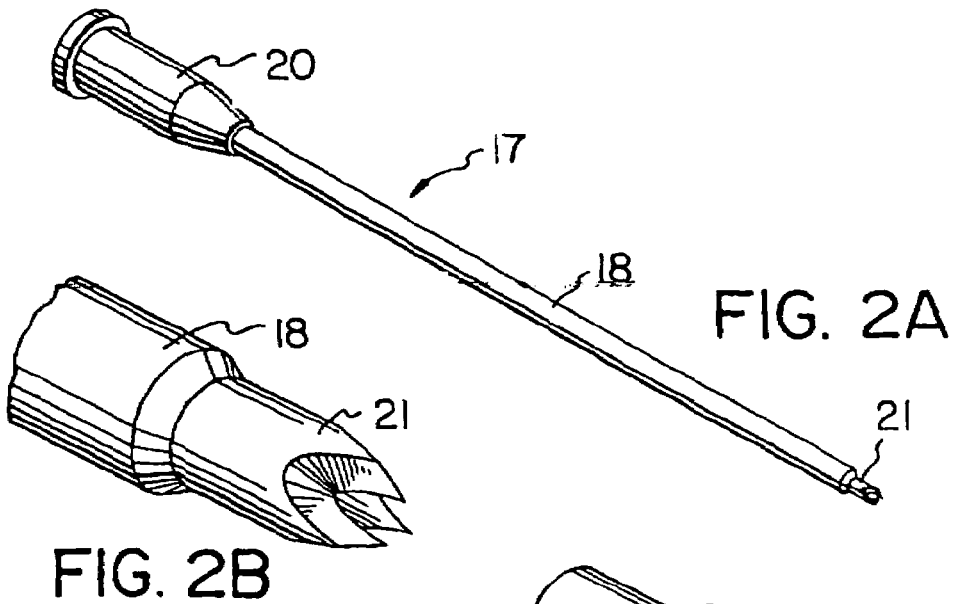
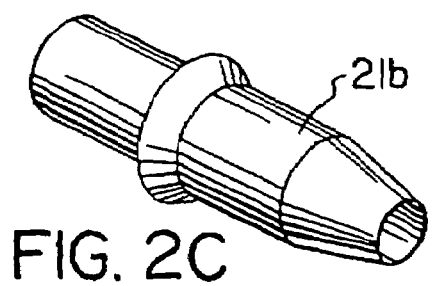
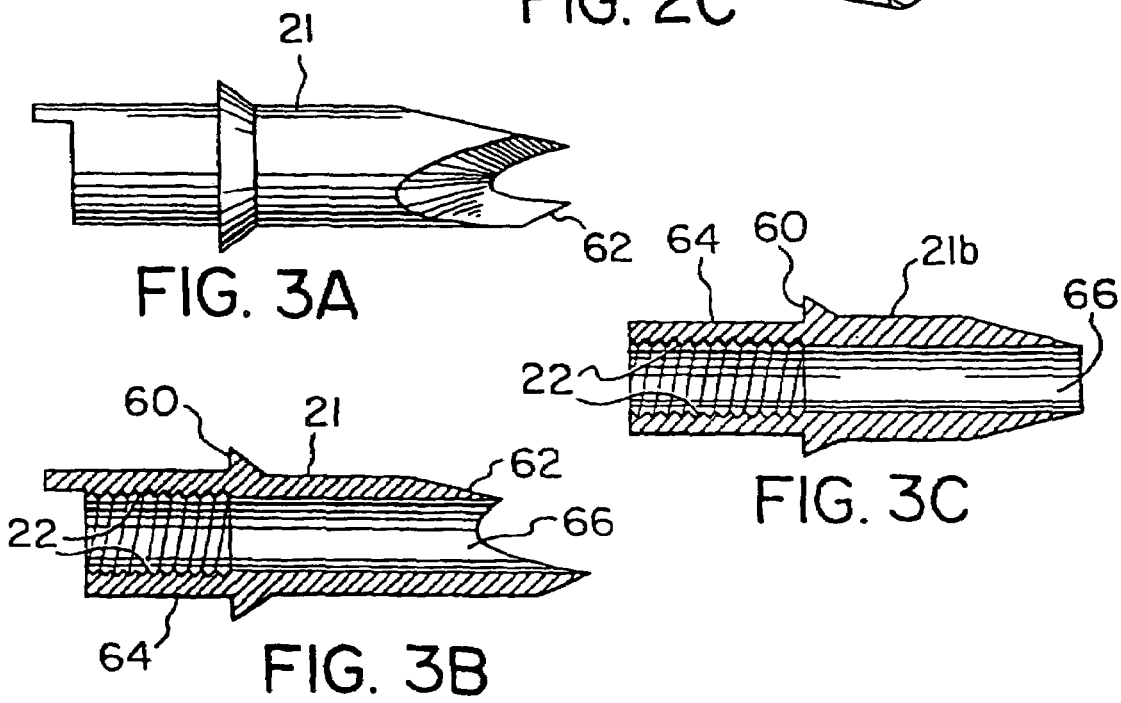

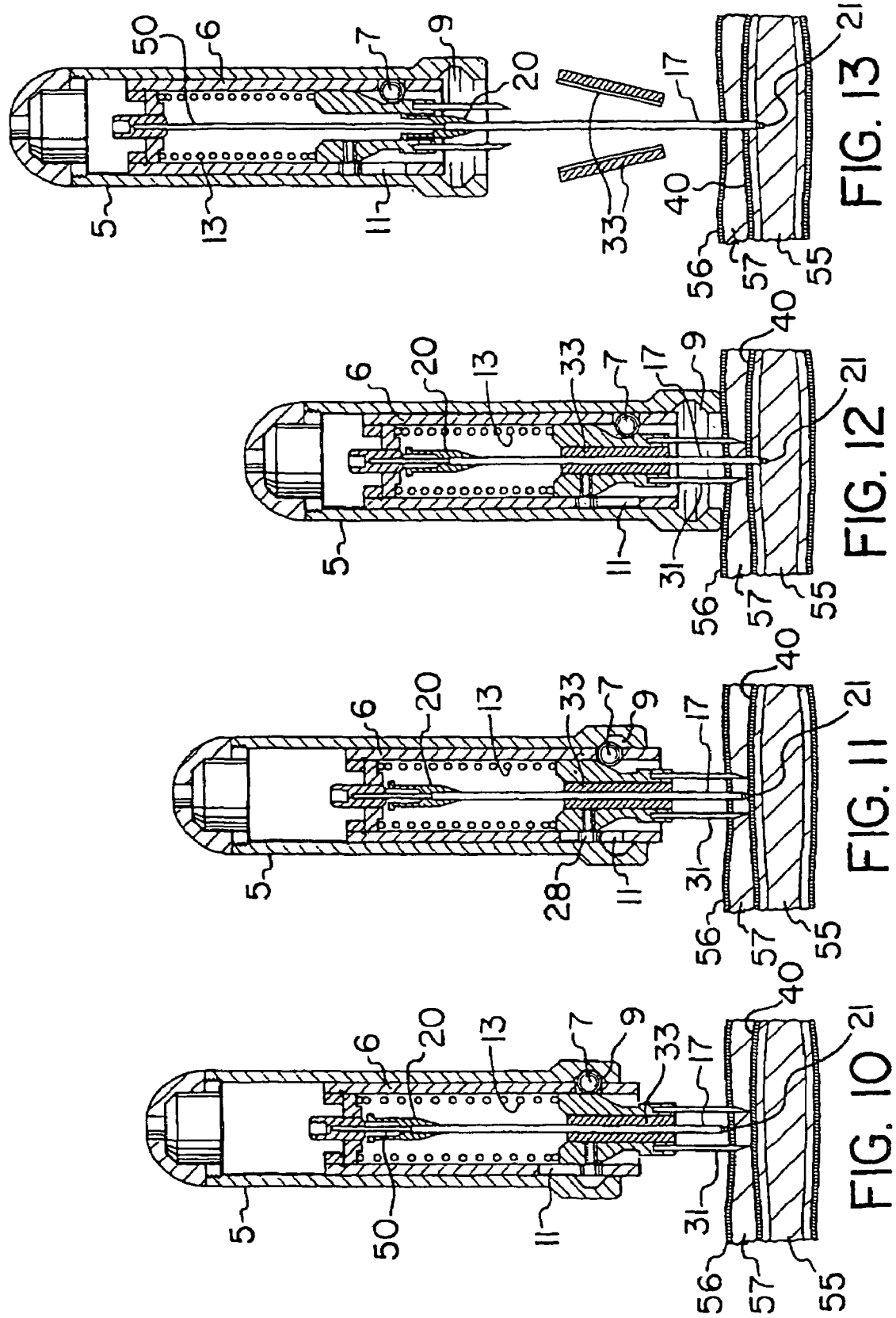

PATCH FOR LOCATING A TARGET ZONE FOR PENETRATION

RELATED APPLICATION

This application is a division of U.S. patent application Ser. No. 09/423,855 which was filed on Mar. 2, 2000 now U.S. Pat. No. 6,761,726.

FIELD

The present invention relates to an apparatus for locating a target site for intraosseous infusion and aspiration, and relieving strain on and preventing dislodgement of an infusion tube used in the intraosseous infusion and aspiration. In particular, the present invention pertains to an apparatus which assists with infusion and aspiration of the bone marrow from humans and animals under emergency and field conditions

BACKGROUND OF THE INVENTION

Usually drugs and liquids are delivered to patients through a catheter or intravenously in a peripheral blood vessel. This method is satisfactory in cases where the blood pressure of the patient is at normal levels. However, when blood pressure drops, for example, during a heart attack, drug overdose, or severe hemorrhaging, the peripheral blood vessels collapse and access to these vessels is difficult or impossible. In such cases, an alternative to intravenous infusion is intraosseous infusion. An intraosseous infusion apparatus may be used to infuse drugs and other liquids into the bone marrow under such emergency conditions. In particular, an intraosseous device is used to penetrate the patient's skin, the subcutaneous layer between the skin and the top of the cortical layer of the bone, the cortical layer of the bone, and the bone marrow, and to supply drugs or fluids directly to the blood supply system of the bone. Typically, the sternum, femur, tibia or other bone near the skin is used. Intraosseous infusion can also be used on patients with blood vessels that are hard to find and on young children whose blood vessels are small and also hard to find. Intraosseous infusion can also be used in emergency or battlefield conditions where quick intravascular access may make the difference between life and death. The caregivers in these situations have low levels of training and need an intraosseous device that is simple and rapid to use.

Although intraosseous infusion is a feasible alternative to intravascular infusion, it has not met with widespread acceptance and popularity for a variety of reasons. One reason for this is the practical difficulty in inserting the infusion needle to the proper depth in the bone in order to access the marrow. One method to overcome this problem has been to use a stop or marker on the needle to indicate when the needle has penetrated to a particular depth. This method has not been effective since it requires an estimation of the required depth and careful control during advancement of the needle. Skin and tissue thickness overlying the bone range from 3 mm to 30 mm and thus the skin surface cannot be used as a reliable reference point. A trained individual like a doctor would be needed to determine the correct depth and insert the intraosseous device. This can be difficult even for highly skilled professionals. Another method to overcome this problem has been to monitor the resistance to the penetration of the infusion needle. The resistance is high when the needle goes through the cortical layer of the bone but decreases when it hits the bone marrow. This method is not very effective since resistances may vary. Again, a highly trained individual is required to advance the intraosseous needle or tube slowly and feel for the changes in resistance.

Intraosseous penetration of the cortical layer of the bone to the bone marrow is also needed when a sample of bone marrow from a patient must be taken. Again a needle or tube must be inserted through the subcutaneous layer into the bone so that the bone marrow can then be aspirated. Again, only a highly trained individual can accurately determine the depth of the penetration of the tube or needle into the bone marrow.

In U.K. Pat. No. 1,315,796, issued to Pashenichny et al., a device for intraosseous injection is disclosed consisting of an outer tube with a screw and a male thread on one end and an inner tube fitted into the outer tube. The device is drilled into the osseous tissue, the inner tube is removed and a cannula is connected to the outer tube. U.S. Pat. No. 4,969,870, issued to Kramer et al., discloses an apparatus for intraosseous infusions having a base positioned with its lower surface against the patient's skin and the infusion tube is pushed through the skin and then rotated to thread through the bone until continued rotation of the tube no longer advances the tube. In both of these devices, there is no automatic depth sensing mechanism. In U.S. Pat. No. 3,815,605, issued to Schmidt et al., an intraosseous device has pins or legs similar to a bone probe that penetrates through the subcutaneous layer. The user releases a compressed spring that exerts a force on and delivers energy to a striker pin to cause it to penetrate the bone. A striker-pin holder that couples the spring to the striker pin, engages a shoulder, which houses the bone probe, thereby limiting the penetration of the striker pin into the bone. Once the spring is released there is no user control over force applied to the striker pin. Thus, if the spring force is insufficient to penetrate the bone cortical the device becomes inoperative. Although this device does have a bone probe which allows the bone cortical layer to be used as a reference point in determining the depth of the penetration of the striker pin instead of the skin, there is no automatic release mechanism to prevent overpenetration of the bone marrow by the coupling member. When the striker-pin holder engages the shoulder, the excess energy released from the spring may drive the coupling member downwardly and over-penetrate the bone.

U.S. Pat. No. 5,520,650 issued to Zadini discloses a device for inserting a cannula into a body cavity. A piston is pushed by hand so that an attached cannula penetrates the skin. Once well under the skin the operator releases the piston and the piston is urged to return by a spring bias creating a vacuum in the piston chamber. The vacuum draws body fluid into the cannula and piston chamber until the vacuum drops. With the vacuum low enough, the piston moves back against an arrest pin releasing an interface member to be urged forward by a spring causing an arrest rod to be locked which, in turn blocks further movement of the catheter or needle. Zadini requires a hollow cannula be inserted since it senses pressure in order to hold the cannula from causing the chain of events that locks an arrest rod and prevents further insertion of the hollow cannula. The needle tip is expected to encounter a fluid which will flow into the needle, destroying the vacuum in the chamber and allow the piston to move, thus triggering the arrest mechanisms of the device. Zadini also requires that the overlying tissue have sealing qualities. Thirdly, Zadini arrests movement of the cannula immediately upon entry into a suitable body cavity and does not detect relative position within a target cavity, but merely whether the cannula is in the cavity or not.

U.S. Pat. No. 4,874,380 issued to Hesketh discloses a releasable catheter retaining device mounted on a patch which has a post to which is anchored a cable tie. The cable tie is used to engage a catheter. The sole function of the patch is to retain a catheter.

Battenfield discloses a template for instructing proper insertion of a means for draining a distended bursa. The template is for use on either a right or left knee and has locating indicia marked on it for visual alignment with the patella and tibia. Since visual alignment alone is unreliable it would be desirable to combine such a method with a more mechanical method of alignment.

Other similar apparatus for intravascular infusion (U.S. Pat. No. 5,527,290 issued to Zadini et al. and U.S. Pat. No. 5,480,388 issued to Zadini et al.) and tracheotomies (U.S. Pat. No. 4,556,059 issued to Adamson, Jr.) may have automatic trigger mechanisms that use a spring for self-propelled insertion. None of the prior art discloses a release mechanism that controls the depth of penetration of the penetrating means inserted at arbitrary speed through arbitrary thickness of overlying tissue, against an unknown resistance.

Another problem in employing intraosseous infusion is the need for quickly and easily finding the proper location on a patient's body for insertion of the infusion tube. A semi-skilled caregiver in an emergency situation would not be able to quickly identify the target location for intraosseous infusion. Prior art discloses templates for guiding the insertion of syringes for draining the bursa of the knee and for insertion of spinal marker needles. A template for guiding a caregiver to the correct location for draining the bursa of the knee along with the hypodermic needle used in the process is disclosed in U.S. Pat. No. 5,364,361, issued to Battenfield. U.S. Pat. No. 4,985,019, issued to Michelson, teaches a X-ray marker disc with a grid pattern and indicia for determining the location and orientation of the spinal marker needle. There is a need for a template to guide the placement of an intraosseous infusion apparatus so that a semi-skilled caregiver can accurately and very quickly determine the site of intraosseous infusion.

A third problem with intraosseous infusion is that strain and stress on the infusion tube that protrudes above the skin may cause dislodgment of the tube from the bone, tearing of the skin or overpenetration of the infusion tube. One cause of such stress is the movement of skin and tissue which may cause strain on the infusion tube and may dislodge it. The infusion tube may be placed under tension by the intravenous fluid supply tube. Forces or pressures from objects pressing on the intraosseous infusion site may push the infusion tube too far into or through the bone. This problem is particularly difficult when a patient is being transported in an ambulance or in a war zone where movement of the patient under uncontrolled conditions is required.

Prior art discloses several devices for supporting catheter tubing, for example U.S. Pat. No. 4,397,641, issued to Jacobs, which teaches a catheter support member and U.S. Pat. No. 5,456,671, issued to Bierman, which teaches a catheter anchoring system. Prior art also discloses several protective coverings for the catheter infusion sites as in U.S. Pat. No. 5,074,847, issued to Greenwell et al., which discloses a shielding device and a method for holding a heparin lock secured to a catheter and U.S. Pat. No. 5,449,349, issued to Sallee et al., which discloses an intravenous tubing cover/protector. These supports are customized for catheters. Thus, a need for an intraosseous tube support which can create a protective loop of slack, and a protector covering the intraosseous infusion site and intraosseous infusion tube exists.

It should therefore be appreciated that there is a significant need for an intraosseous infusion or aspiration apparatus and a related method that can be used quickly and easily by even low-skilled caregivers in emergency or field conditions. Further there is needed such a device that provides for quick positioning of the target area and one that enables semi-skilled users to reliably and accurately position an intraosseous infusion device. There is also a need for such a device that provides relief from the stress and strain placed on the tubing and protection against dislodgment or overpenetration.

SUMMARY OF THE INVENTION

According to the invention, there is provided an apparatus for intraosseous fluid infusion and aspiration of bone marrow beneath a bone cortical layer of a patient. The apparatus has an operative end that refers to the bone penetrating end of the apparatus and a remote end opposite to the operative end. The apparatus has a housing assembly, comprising inner and outer sleeves, spring assembly, a bone probe assembly, a release mechanism, and a coupler. The housing assembly is operative to receive a force directly applied by a user. The coupler is operative to couple the force applied by the user to an infusion tube such that the force directly applied by the user drives the infusion tube through the bone. The infusion tube may have a bone portal and a hollow flexible tube affixed to the bone portal. The infusion tube infuses fluid to and aspirates tissue from the bone marrow. The release mechanism removes substantially all of the force directly applied by the user on the infusion tube once the bone portal has penetrated the bone marrow a predetermined distance.

The spring assembly is comprised of a spring that is compressed between the remote end of the inner sleeve and the remote end of the bone probe assembly, and functions to hold these two parts in a relative initial position.

The bone probe assembly is slidable into the housing assembly. As a user exerts force onto the housing assembly, the spring compresses and the bone portal penetrates the bone cortical layer. When the housing is withdrawn, the infusion tube is left in the body of the patient with the bone portal embedded in the bone marrow and the hollow infusion tube extending out of the skin.

The housing is, further, comprised of a cylindrical outer sleeve with a ball race in an interior surface at the operative end of the sleeve and a cylindrical inner sleeve which is slidably insertable in the outer sleeve. The inner sleeve has a plurality of ball holes circumferentially spaced in the operative end of the sleeve such that the inner and outer sleeve can be coupled through a plurality of balls located partly in these ball holes and partly in the ball race of the outer sleeve.

Specifically, the bone probe assembly is removably insertable in the inner sleeve. A portion of the outer surface of the bone probe assembly is conical in shape, decreasing in diameter towards the operative end of the infusion apparatus. When a user applies a force to the outer sleeve, the balls couple the outer sleeve to the inner sleeve, which couples the outer sleeve to the infusion tube through a long slender stylet coupled to the remote end of the inner sleeve and over which the hollow infusion tube is mounted. As the user applies force to the outer sleeve, the entire apparatus moves towards the patient and the needles of the bone probe penetrate the skin and subcutaneous layers until they come to rest on the cortical layer. As the user continues to apply force to the outer sleeve, all parts of the apparatus, except for the bone probe assembly, continue to move toward the patient and the bone portal begins to penetrate the cortical layer. Because the bone probe assembly is in contact with the cortical layer and is slidable in the inner sleeve, the bone probe assembly does not move toward the patient. As more relative motion occurs between the bone probe assembly and the rest of the apparatus, the balls start to move down the conical outer surface of the bone probe assembly, and thus move radially inward. When the infusion tube has penetrated the correct distance into the cortical layer, the balls have moved inward until they no longer couple the outer sleeve to the inner sleeve. This action is the release mechanism which releases the outer sleeve from the rest of the apparatus. At this point, any downward force exerted by the user to the outer sleeve, is not transferred to the infusion tube, thereby preventing any further penetration of the infusion tube into the bone.

The bone probe assembly is also coupled to the inner sleeve through pins that engage pin slots in the inner sleeve. The pin slots allow a displacement of the bone probe assembly relative to the inner sleeve that is slightly beyond the displacement at which the release mechanism is activated. The pins are located in pin holes in the annular band of the bone probe assembly adjacent to the remote end of the conical surface down which the balls travel as the release mechanism is activated. A bone probe ring is adjacent to the operative end of the conical surface. From the bone probe ring, a plurality of needles project out in a circle.

Furthermore, the bone probe assembly has an axial opening. In the axial opening there may be an infusion tube surrounded by two support sleeves and mounted on a stylet attached to the inner sleeve and passing through the infusion tube and contacting a bone portal. The support sleeves brace the infusion tube and stylet when a force is applied to the outer sleeve. The stylet transfers user applied force to the bone portal to cause it to penetrate the bone.

In another aspect of the invention, a release mechanism is provided. This release mechanism is designed to control the distance over which a user exerted force can act. The displacement of the bone portal relative to the bone is always identical regardless of the speed at which the force is exerted by a user, regardless of whether the force exerted by a user is constant or variable, and regardless of the magnitude of the force exerted on the bone portal. This is in contrast to a spring trigger mechanism where the apparatus is propelled forward by a fixed quantity of energy stored in a spring but the distance propelled cannot be accurately controlled because the fixed amount of energy stored in the spring may be either inadequate to puncture the bone, or may be too much, resulting in overpenetration of the bone.

In another aspect of the invention, the intraosseous infusion and aspiration apparatus may be optimized for infusion and aspiration of different bones with different bone resistances, different overlying skin and subcutaneous resistances, and different depth of penetrations by modifying several variables. The spring constant, the attributes of the bone probe needles, the axial displacement of the balls, the angle of the conical surface on the bone probe assembly, the angle of the ball contacting surface on the outer sleeve and the size of the pin slots may be adjusted to yield different bone penetration depths, different maximum penetration depths, different applied force, and different maximum applied force that would be needed for different bones.

Accordingly, the present invention is embodied in an intraosseous infusion and aspiration apparatus and related method which effectively allows a user to place an infusion tube in the bone marrow of the patient without having to estimate the penetration depth or bone's resistance to penetration and without having to estimate the target area of the placement of the infusion tube. Essentially, the present invention provides an object to be positioned, an outer sleeve to push on, a coupler to couple the outer sleeve to the object being positioned, a position probe that senses the location of the object to be positioned relative to a reference point and a release mechanism that removes substantially all of the force applied to the object, once the object is correctly positioned relative to the reference point. More specifically, the object being positioned is the infusion tube, the coupler is the balls, and the position probe corresponds to the bone probe assembly.

There may be additionally provided an elongated remover in the shape of a rod that has threads at one end. After an infusion is complete, the remover is inserted into the infusion tube so that it engages the threads in the bone portal. A force is applied to the remover in the direction away from the bone thereby extracting the bone portal from the bone.

In another aspect of the invention, there is provided a template patch for locating the target site for intraosseous infusion and aspiration. The target patch has a curved finger engaging recess and a target zone that is a predetermined distance from the curved finger engaging recess. The user's finger is used to align the template patch by palpating a key anatomical of the bone to be infused and engaging the curved finger engaging recess with the finger of the user so that the target zone is positioned over the desired area of penetration and infusion.

The template patch serves a second function in relieving strain on the infusion tube. The flexible template has a tube clamp that can clamp an infusion tube or a second tube connected to the infusion tube to lessen the strain and decrease the effect of external forces on the infusion tube. The tube clamp a loop of slack in the flexible infusion tube. Since the underside of the template patch has an adhesive lining, the template patch can be fastened onto the skin of the patient. The periphery of the template patch has a fastening material that engages with a fastening material of a covering that protects the infusion tube from dislodgment. The covering may be in the shape of a hard, transparent dome.

In another aspect of the invention, a method for using the intraosseous infusion and aspiration apparatus may comprise using the template patch to quickly locate the site of infusion by first identifying a key anatomical feature of the bone to be penetrated. The curved finger engaging recess of the template patch is engaged with a finger that is palpating this feature so that the target zone is over the desired area of penetration. An intraosseous fluid infusion and aspiration apparatus may be introduced to the target zone and by pushing on the outer sleeve of the apparatus with sufficient force, the bone portal is inserted into the bone marrow to a predetermined depth. The apparatus may be pulled out after the release mechanism is heard or felt and leaves behind the infusion tube and the bone portal in the bone. An external tube may be connected to the infusion tube and then clamped to the tube clamp located on the template patch to lessen the strain on the infusion tube or, the infusion tube may be clamped directly in the tube clamp. A covering may be placed on the template patch to protect the infusion site. After the infusion is complete, the bone portal and infusion tube may be removed with a remover that engages the bone portal.

BRIEF DESCRIPTION OF THE DRAWINGS

The novel features believed to characterize the invention are set forth in the appended claims. The invention, itself, however, as well as other features and advantages thereof, will be best understood by reference to the detailed description which follows, read in conjunction with the accompanying drawings, wherein:

FIG. 2A is a perspective view of an infusion tube with the hollow flexible tube, tube connector and bone portal;

FIG. 2B is a perspective view of the bone portal and a portion of the attached hollow tube;

FIG. 2C is a perspective view of the conically tapered bone portal and a portion of the attached hollow tube.

FIG. 3A is a side elevation view of the bone portal:

FIG. 3B is a sectional view of FIG. 3A;

FIG. 3C is a sectional view of the conically tapered bone portal.

FIG. 10 is the first stage in the use of the intraosseous infusion and aspiration apparatus showing the bone probe against the bone cortical layer and the bone portal just beginning to penetrate the skin;

FIG. 11 is the second stage in the use of the intraosseous infusion and aspiration apparatus showing that the bone portal has penetrated the bone cortical layer;

FIG. 12 is the third stage in the use of the intraosseous infusion and aspiration apparatus showing that the inner sleeve has been released from the outer sleeve leaving the bone portal at the correct depth in the bone marrow;

FIG. 13 is the fourth stage in the use of the intraosseous infusion and aspiration apparatus showing that the apparatus has disengaged from the skin of the patient and the infusion tube has been left in the patient;

DETAILED DESCRIPTION WITH REFERENCE TO DRAWINGS

Figure 1:
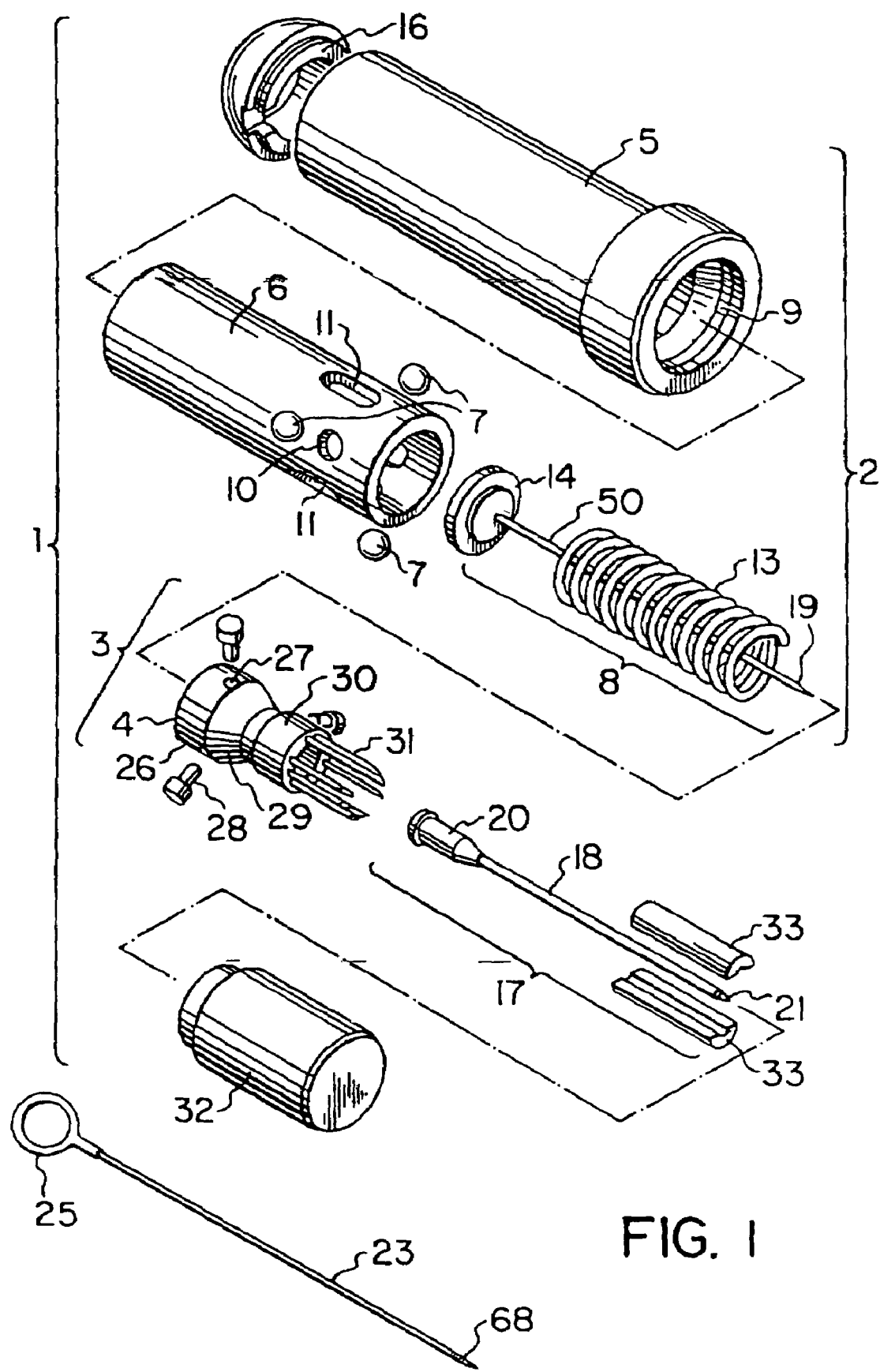
FIG. 1 is an exploded isometric view of the intraosseous infusion and aspiration apparatus.

In the following description it is to be understood that the apparatus has two ends: an operative end that refers to the bone penetrating end of the apparatus and the opposite end referred to as the remote end.

The intraosseous infusion and aspiration apparatus 1 serves as an introducer that introduces an object, an infusion tube 17, to a specific position and a predetermined depth in the bone marrow 55. The introducer is comprised of an outer sleeve 5, a bone probe assembly 3, and a coupler 7 that couples the infusion tube 17 to the outer sleeve 5. Thus the infusion tube 17 is positioned in the bone marrow 55 through the action of an outer sleeve 5, a bone probe assembly 3 that senses the location of the infusion tube 17 that is being positioned, and a coupler 7 that couples the outer sleeve 5 to the infusion tube 17 so that force exerted on the outer sleeve 5 is transferred to the infusion tube 17. The automatic release mechanism of the apparatus involves all parts except for the infusion tube 17.

A cross-section of the intraosseous infusion and aspiration apparatus 1 is shown in its preferred embodiment in FIG. 1. The apparatus has a housing assembly 2, a plurality of balls 7, a spring assembly 8, a stylet 50, stylet mount 48, stylet base 14 and a bone probe assembly 3.

The housing assembly 2 has an outer sleeve 5 and an inner sleeve 6. The hollow outer sleeve 5 is cylindrical in shape and serves as the surface to which force is applied. A ball race 9 is formed in the interior wall of the operative end of the hollow outer sleeve 5. The hollow outer sleeve 5 also has a cap 16 with a projection or thread that allows it to fit snugly into the remote end of outer sleeve 5.

The inner sleeve 6, also of cylindrical shape and hollow, slidably fits inside the hollow outer sleeve 5. The inner sleeve 6 has a plurality of ball holes 10 circular in shape and a plurality of elongated pin slots 11 circumferentially spaced about the operative end of the inner sleeve 6.

A plurality of balls 7 serve as the coupler coupling the outer sleeve 5 to the infusion tube 17. The balls 7 couple the outer sleeve 5, to the inner sleeve 6 which is releasably attached to the infusion tube 17. The balls 7 are of a diameter slightly smaller than the ball holes 10 and fit partly in the ball holes 10 of the inner sleeve 6 and partly in the ball race 9 of the hollow outer sleeve 5 coupling the hollow outer sleeve 5 with the inner sleeve 6.

The spring assembly 8 has a helical spring 13 which is positioned inside the inner sleeve 6, abutting a stylet base 14. One side of the stylet base 14 abuts a retaining lip 15 of the interior of the inner sleeve 6 proximate a remote end thereof. On the opposite side, the stylet base 14 has a projection that fits snugly into the remote end of the spring 13. The stylet base 14 couples the compression forces from spring 13 to the inner sleeve 6.

A stylet 50 is connected to a stylet mount 48 (see FIG. 5) affixed to the center of the stylet base 14. Stylet base 14 is coupled to the inner sleeve 6 and the spring 13. The force exerted onto the hollow outer sleeve 5 is transferred to the inner sleeve 6 through the balls 7 coupling the two bodies 5, 6 together and is further transferred to the spring 13 and stylet 50 through the retaining lip 15 and stylet base 14. The stylet 50 is rigid and is inserted into the infusion tube 17 to push the infusion tube 17 into the bone 40.

The infusion tube 17 consists of flexible tubing 18, and a bone portal 21. The flexible tubing 18 is a hollow, elongated, flexible tube connected to a tube connector 20 (FIG. 2A) at the remote end. Referring to FIGS. 2A and 2B, the flexible tubing 18 is connected to the bone portal 21. The flexible tubing 18 is attached to the bone portal 21 providing a fluid passageway from the flexible tube 18 to the bone portal 21. Referring to FIGS. 2A, 2B, 2C, 3A, 3B and 3C, the bone portal 21 is made of a rigid material such as stainless steel and has a bore 66 which communicates with an opening at its operative end to allow the infusion of fluid into the bone marrow. On the interior surface of the bore 66 are threads 22. An annular shoulder 60 serves as a stop for the hollow, flexible tubing 18 that is attached to the exterior surface of the bone portal 21. The end of the bone portal 21 is beveled to form sharp points 62. Alternatively, as seen in FIGS. 2C and 3C, the bone portal 21b may be conically tapered.

As seen in FIG. 1, the remover 23 has a slender rod threaded at its end with threads 68 dimensioned to register with the threads 22 on the interior bore of the bone portal 21 and a handle 25 at the remote end is used to remove the flexible tubing 18 and bone portal 21 from the bone marrow after the infusion is complete.

Referring to FIG. 1, the intraosseous infusion and aspiration apparatus 1 further includes a bone probe assembly 3 that serves as a position probe allowing the location of the object, the infusion tube 17, to be positioned relative to a reference point. The bone probe assembly 3 comprises a bone probe ring 4, a plurality of pins 28, and a plurality of needles 31. The bone probe ring 4 comprises an annular band 26 that is dimensioned to slide into one end of the inner sleeve 6. This annular band 26 of the bone probe ring 4 has a plurality of pin holes 27. A plurality of pins 28 can be put through these pin holes 27 and into the elongated pin slots 11 in the inner sleeve 6 further slidably securing the bone probe assembly 3 to the inner sleeve 6. The bone probe ring 4 also has a conical surface 29 (a ramp in transverse drawings) adjacent to the annular band 26. A ring of needles 31 protrude out from the operative end 30 of bone probe ring 4. There is a protective covering 32 that covers the needles 31 to protect an administrator from accidental contact with the needles 31.

The bone probe needles 31 serve as a reference for the measurement of the distance through the bone that the bone portal 21 has penetrated since the needles 31 penetrate the skin and subcutaneous layers overlying the bone, but do not penetrate the bone.

The intraosseous infusion and aspiration apparatus 1 further includes longitudinally split support sleeves 33 located in the bore of the bone probe ring 4. Support sleeves 33 brace the stylet 50 so that it does not buckle under the force applied to it to penetrate the bone.

Figure 4:
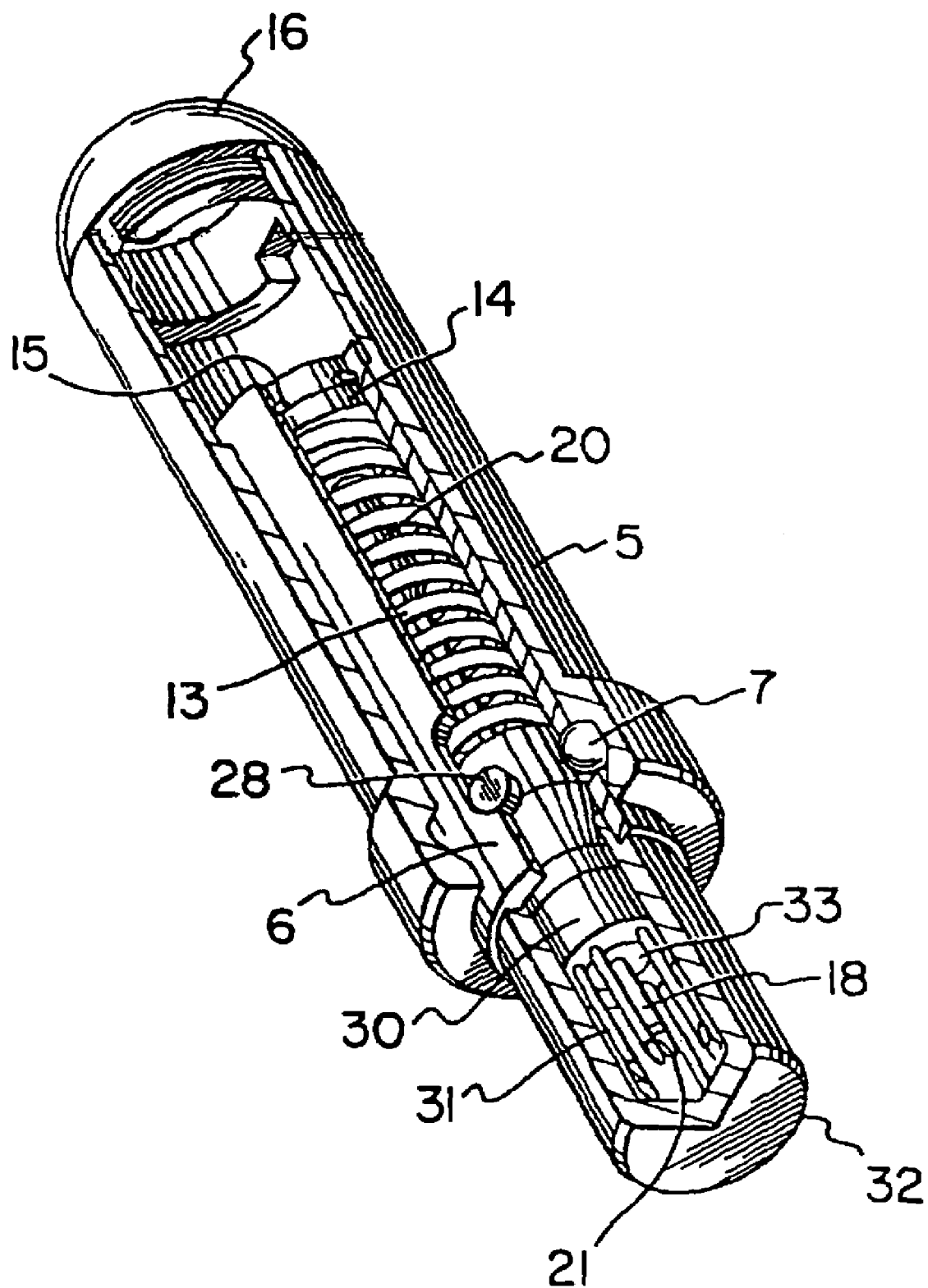
FIG. 4 is a cut-away perspective view of the assembled intraosseous infusion and aspiration apparatus.

Referring to FIG. 4, the assembled intraosseous infusion and aspiration apparatus 1 is shown in its position before use with a protective covering 32 over the bone probe needles 31.

The intraosseous infusion and aspiration apparatus 1 can be optimized for infusion of different bones such as the sternum, the proximal and distal ends of the tibia, the femur, and the clavicle. These bones have different resistances to penetration thus the amount of force needed to insert the apparatus in the bone marrow of the bones may differ. Also, since different depths of penetration of bone to reach the bone marrow may be needed for different bones, the bone penetration distance of the bone portal may need to be adjusted. In addition, the skin and subcutaneous layers overlying the different bones may differ in thickness and their resistance to penetration. The bone probe ring 4 and spring 13 may have to be adjusted to compensate for these changes in the thickness and resistance of the skin and underlying tissue. The intraosseous infusion and aspiration apparatus 1 may also be customized for pediatric patients who usually have smaller bones with lesser resistance to penetration.

One feature of the intraosseous infusion and aspiration apparatus 1 that can be adjusted is the spring force applied to the bone probe ring 4. The tips of the bone probe needles 31 serve as a reference point to determine the depth of penetration of the bone portal 21 through the cortical bone layer 40 and bone marrow 55. The magnitude of the spring force needed to force the bone probe needles 31 to penetrate the skin 56 and subcutaneous layer 57 so that it abuts the bone cortical layer 40 is dependent on the bone probe needle 31 configuration, the type of tips of needles 31, the size and the number of needles 31, and the resistance of the skin 56 and subcutaneous layer 57. For example, if the number of needles is decreased then a weaker spring force may be used for the bone probe needles 31 to penetrate the same skin and underlying tissue. Since different anatomical sites have different resistances in the skin and underlying tissues, the spring force and the bone probe needles 31 can be adjusted to obtain optimum characteristics for the penetration of the bone probe needles 31 to the cortical bone 40.

Figure 5:
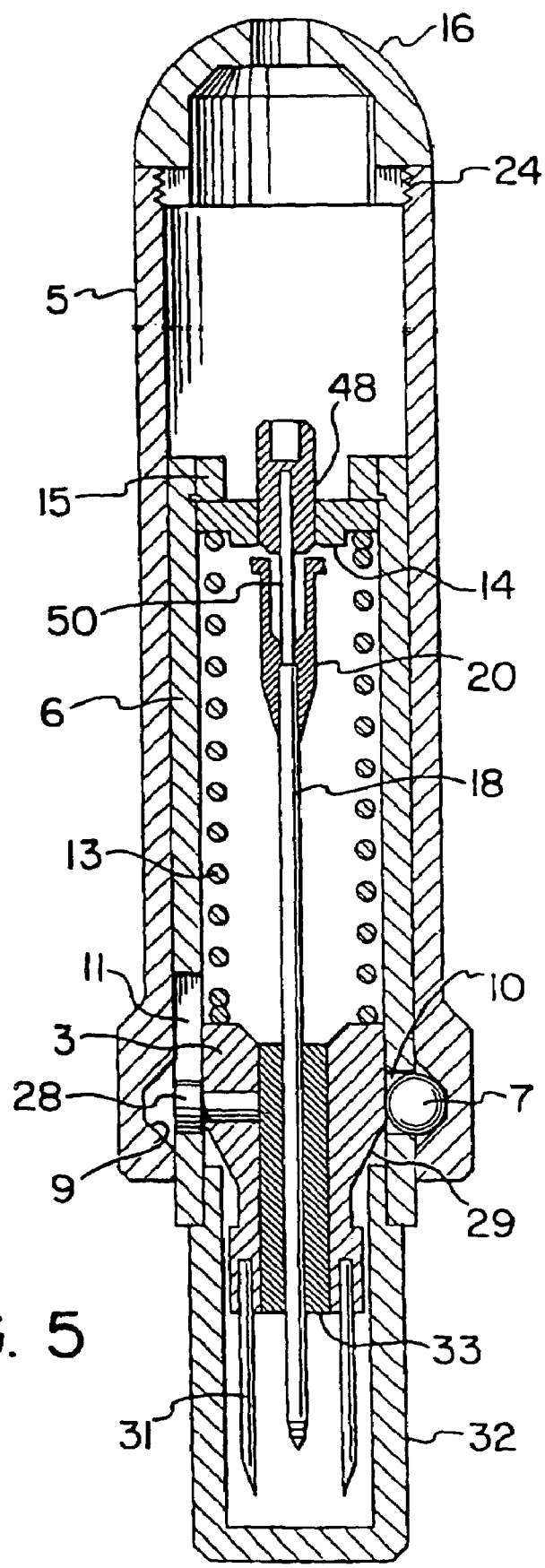
FIG. 5 is a sectional view of the intraosseous infusion and aspiration apparatus.
Figure 6:
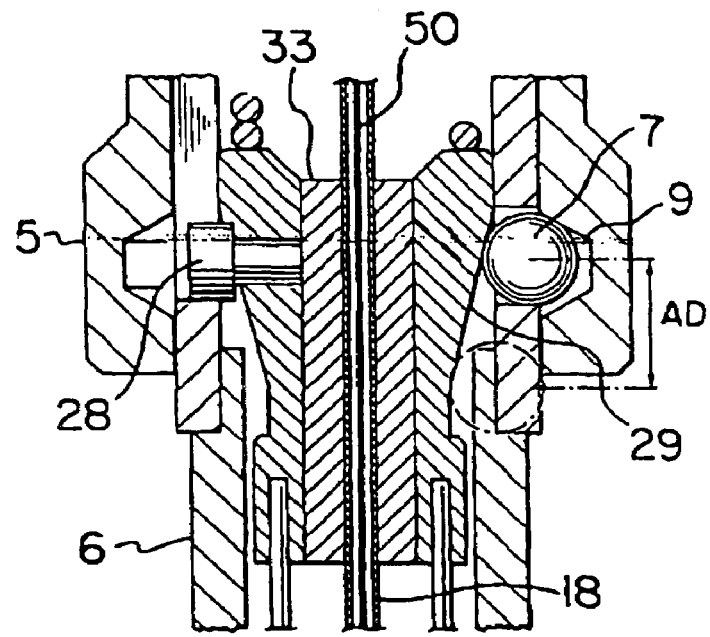
FIG. 6 shows the axial and radial displacement of the ball during release.

Another feature of the apparatus 1 that can be adapted is the release mechanism. Referring to FIG. 5, the ball release mechanism comprises a plurality of balls 7, the ball race 9, the ball holes 10, the spring assembly 8 and the conical surface 29 of the bone probe ring 4 and the bone probe assembly 3 itself. Referring to FIG. 6, the starting position of the ball 7 before release is on the remote end and the ending position of the ball 7 is proximate the operative end of the conical surface 29 of the bone probe ring 4.

Figure 7:
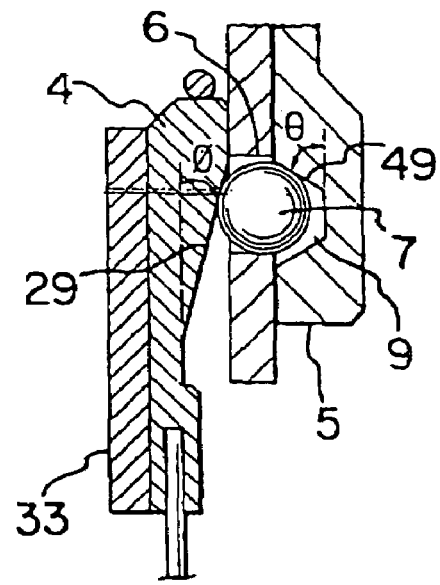
FIG. 7 shows the angles on the ball race and the tapered surface of the bone probe assembly in an example of a release mechanism of an intraosseous infusion and aspiration apparatus.

Referring to FIG. 7, the angle of the conical surface 29 on the bone probe ring 4, the angle of the ball contacting surface 49 of the ball race 9 and the spring force can be adjusted to determine the maximum bone portal penetration force available to insert the infusion tube 17 to a predetermined depth. For example, if the angle of the conical surface with the axis of the bone probe assembly $\phi$ (see FIG. 7) is increased for a constant ball race contacting surface angle $\theta$ and constant spring constant, the maximum available bone portal penetration force will decrease. If the angle $\theta$ is increased as angle $\phi$ and the spring constant are kept constant, the maximum available bone portal penetration force will increase. If the spring constant is increased for constant angle $\theta$ and angle $\phi$, the maximum available bone portal force will increase. If this maximum bone portal force is exceeded, the apparatus 1 is released without damage. Since this force is much less than the force at which mechanical failure occurs, the apparatus will not be damaged and the patient will not be injured.

Figure 8:
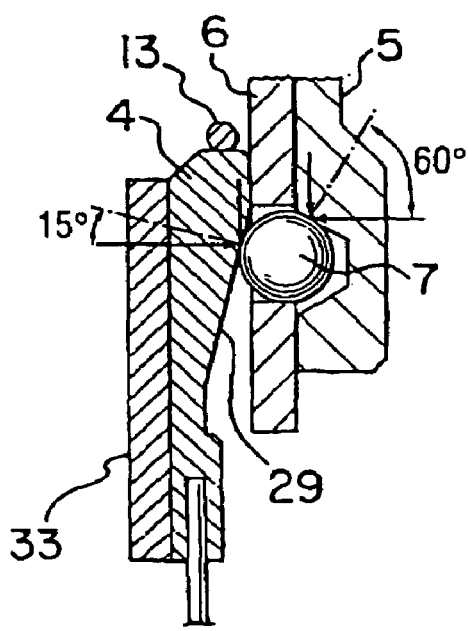
FIG. 8 shows the forces acting on the ball, inner sleeve, and outer sleeve during an initial phase of the release mechanism.
Figure 9:
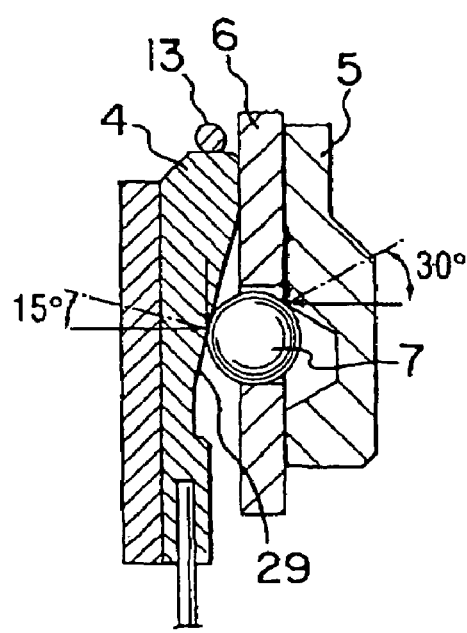
FIG. 9 shows the forces acting on the ball, inner sleeve, and outer sleeve during a late phase of the release mechanism.

FIG. 8 shows the forces on the ball release mechanism in an initial phase where the ball is positioned at the remote end of the conical surface 29 of the bone probe ring 4. In this initial phase, forces up to the maximum force may be applied without premature release. FIG. 9 shows the forces on the ball release mechanism as the balls are positioned in the operative end of the conical surface 29 of the bone probe ring 4. In this late phase, the apparatus 1 may release prematurely since there is a greater horizontal force acting on the ball 7 forcing the ball 7 onto the ramp 29. The horizontal force tends to push the bone probe up and causes release. In this phase, the axial displacement of the bone assembly relative to the inner sleeve 6 is determined by the angle $\phi$, the angle $\theta$ and the diameter of the balls 7. Changing one of these design variables will change the axial displacement that occurs in this phase.

Another aspect of the intraosseous infusion and aspiration apparatus 1 that can be adjusted is the size of elongated pin slots 11 (see FIG. 10-13) in the inner sleeve 6 proximate the operative end. These pin slots 11 determine the maximum axial displacement of the bone probe assembly 3 in relation to the inner sleeve 6. Because the infusion tube 17 is coupled to the inner sleeve 6, these pin slots 11 also determine the maximum penetration depth of the infusion tube 17 in relation to the bone probe needles 31. Thus, if there is a failure in the release mechanism, this feature ensures that the bone portal 21 does not over-penetrate the bone marrow and cause injury to the patient.

The ball race 9 allows for rotational decoupling between the hollow outer sleeve 5 and the inner sleeve 6. Optionally, ball race sections could be provided in order to provide limited decoupling between the hollow outer sleeve 5 and the inner sleeve 6. With such a feature, if the needles 31 were decoupled by use of a bearing on the bone probe assembly for example, it would be possible to apply torque to the bone portal 21 in order to assist its penetration into the bone. Alternatively, other methods may be used to couple the outer sleeve 5 to the inner sleeve 6, such as a pin in outer sleeve 5, engaging a slot of inner sleeve 6.

The operation of the intraosseous infusion and aspiration apparatus 1 and its release mechanism is shown in FIGS. 10, 11, 12, 13. The apparatus 1 contains a release mechanism for disconnecting the infusion tube 17 and the bone portal 21 from the outer sleeve 5 when the bone portal 21 is at a specific depth relative to the outer surface of the cortical bone 40 thereby preventing the bone portal 21 from penetrating beyond the bone marrow 55 and out the opposite cortical layer of the bone. Specifically, the intraosseous infusion and aspiration apparatus 1 is placed on the target location perpendicular to the skin of the patient. A force is applied so that the bone probe needles 31 go through the skin 56. A portion of the bone portal 21 also enters the subcutaneous layer 57 (see FIG. 10).

Referring to FIG. 10, the balls 7 are in the ball holes 10 and ball race 9. The pins 28 sit at the operative end of the elongated pin slots 11. As more force is applied on the hollow outer sleeve 5, as seen in FIG. 11, the outer sleeve 5 and the inner sleeve 6 move towards the operative end of the apparatus 1. Since the infusion tube 17 is coupled through the stylet 50 to the stylet base 14 which is coupled to the inner sleeve 6 which in turn is coupled to the outer sleeve 5, as force is exerted on outer sleeve 5, the bone portal 21 penetrates the bone cortical layer 40. Since the bone probe assembly 3 has not changed in position, there is relative movement of the pins 28 on the bone probe assembly 3 towards the remote end of the elongated pin slots 11 of the inner sleeve 6. The balls 7 coupling the inner sleeve 6 to the hollow outer sleeve 5 are allowed to move out of the ball race 9 of the hollow outer sleeve 5 and through the ball holes 10 in the inner sleeve 6 toward the center of the apparatus since the hollow outer sleeve 5 is moving down relative to the bone probe assembly 3 and space is created into which the balls 7 can move.

As seen in FIG. 12, as more force is applied, the penetration of the infusion tube 17 into the bone marrow 55 takes place. Eventually the balls 7 have traveled radially inward towards the centre of the apparatus sufficiently so that they no longer make contact with the ramp surface 49 of the ball race 9 in the outer sleeve 5. When this occurs (see FIG. 12) force is no longer transferred from the outer sleeve 5 to the inner sleeve 6. At this point, the infusion tube 17 has been released from its coupling to the outer sleeve 5. The infusion tube 17 has been inserted to the correct depth.

The hollow outer sleeve 5 has been pushed so that the operative end of the hollow outer sleeve 5 rests on the skin of the patient. The balls 7 have moved out of the ball race 9, through the ball holes 10, and down the conical surface 29 into the space between the bone probe assembly 3 and the inner sleeve 6, uncoupling the hollow outer sleeve 5 from the inner sleeve 6. Compressed spring 13 exerts a force on the bone probe assembly 3 against the stylet base 14 causing the balls 7 to be pressed outwardly against the outer sleeve 5, thereby producing a frictional force between the outer sleeve 5, the inner sleeve 6 and the bone probe assembly 3. In FIG. 13, the hollow outer sleeve 5 is pulled back, pulling the stylet 50 from the infusion tube 17. The support sleeves 33 fall out as the apparatus 1 is removed. The infusion tube 17 can be connected to another tube 41 or directly to a source of drugs and fluid using the tube connector 20 on the infusion tube 17.

Figure 14:
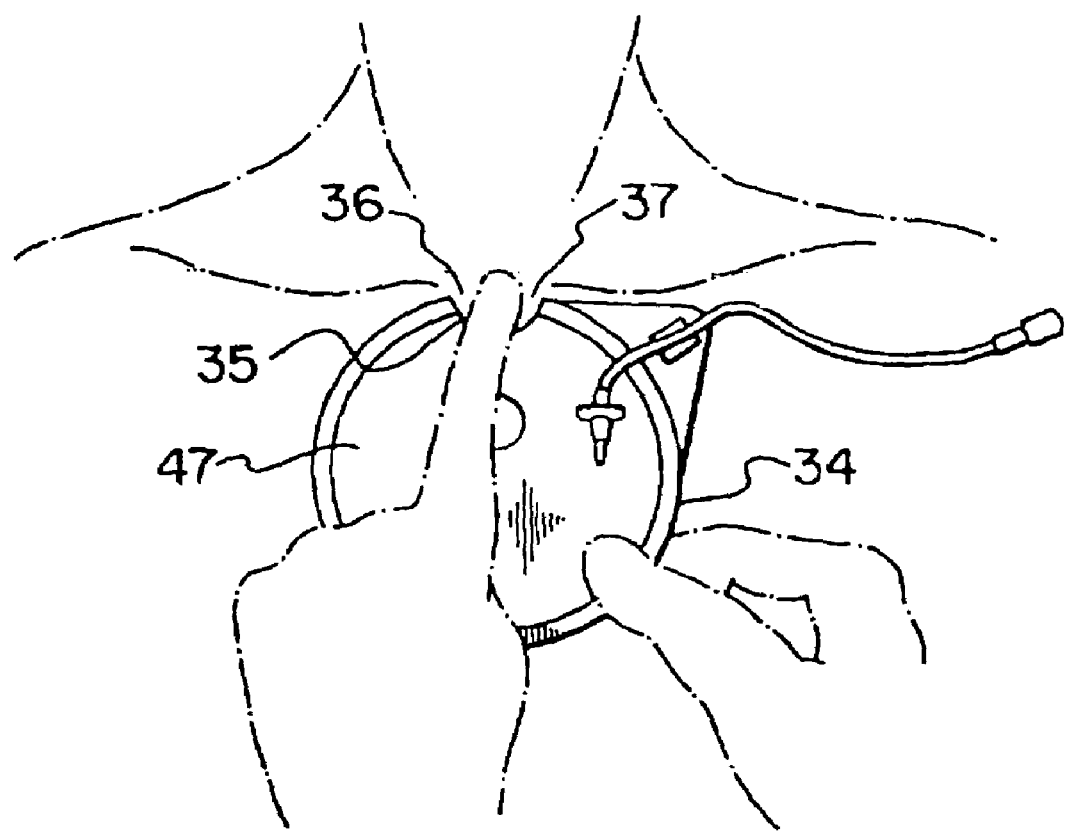
FIG. 14 shows the placement of the template patch on the skin over the patient's sternal bone.

This intraosseous infusion and aspiration apparatus 1 can be used in conjunction with a target/strain-relief patch 34 (FIG. 14). The patch 34 is used as a guide to ensure that the intraosseous infusion and aspiration apparatus 1 is correctly positioned in the proper location on a bone. A prominent anatomical feature of the bone like a notch, a depression, or a bump is used as a reference point to determine the target location for the infusion or aspiration of the bone marrow of flat bones such as the sternum, or iliac crest and long bones such as the femur, the tibia, or the radius.

Figure 15:
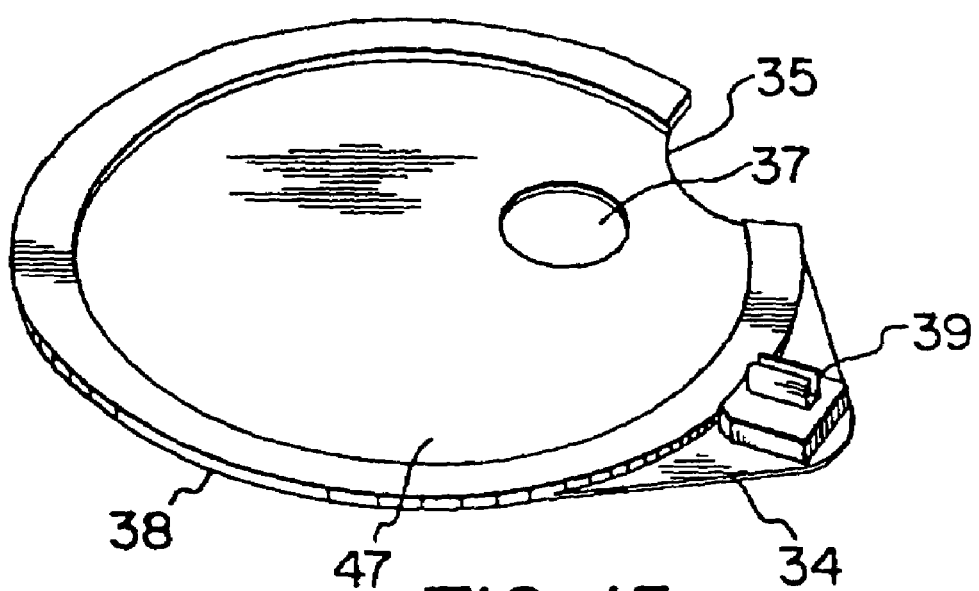
FIG. 15 shows the template patch.

Referring to FIG. 14, the patch 34 includes a patch base 47 which is used to locate a target zone 37 on the manubrium bone of a patient by placing the finger in peripheral notch 35 and at the same time locating the finger in the sternal notch 36 of the patient. Referring to FIG. 15, a target zone 37 in the patch base 47 is positioned a predetermined distance away from the peripheral notch 35. The target zone 37 is used to align the intraosseous infusion and aspiration apparatus 1 with a desired area of penetration of the patient. Also, the patch base 47 has an adhesive underside with a liner 58 that can be peeled to removably fasten the patch base 47 to the skin 56 of the patient. Liner 58 may be split such that it has two pieces that can be removed independent of one another. See, for example, FIG. 17 which shows liner 58 made up of a first piece 58A and second piece 58B.

Figure 18:
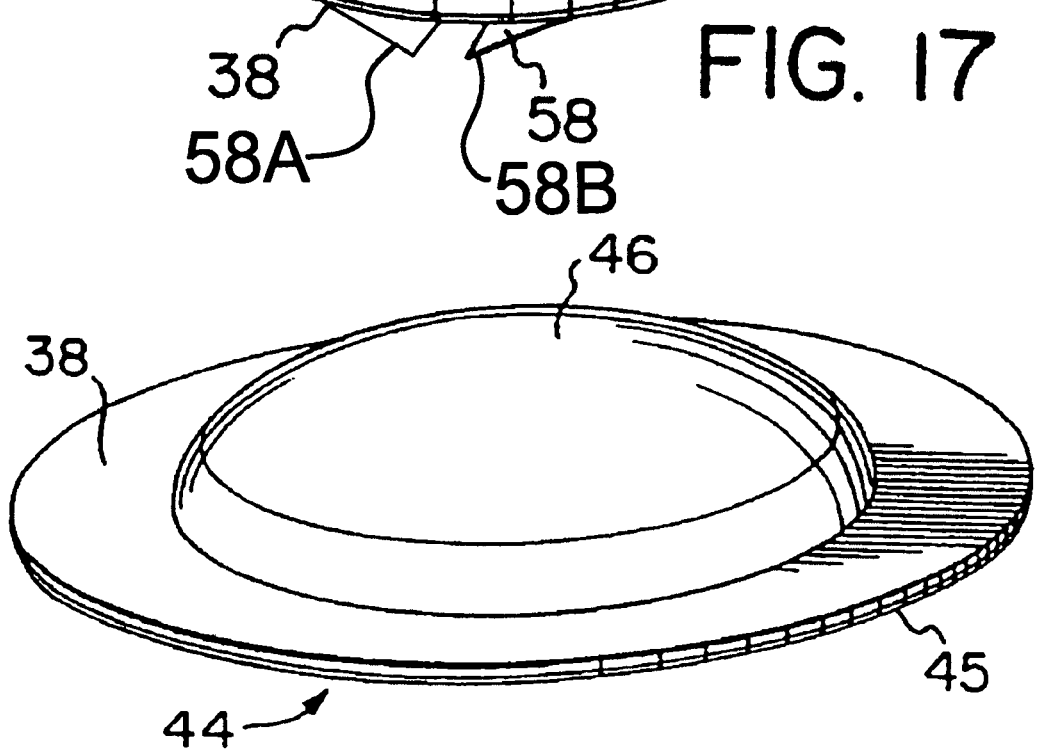
FIG. 18 shows the covering for the template patch.

In addition, a fastening material 38 is present around the periphery of the patch base 47 so that a cover 44 may be placed on it and engage the fastening material 45 (FIG. 18). The patch 34 also has a tube clamp 39 outside the fastening material 45 on an extension of the patch base 47. The infusion tube 17 may be attached by the tube clamp 39 to the patch 34 and then connected to an intravenous tube through its tube connector 20. In another embodiment, a connector tube 41 with a connector 42 and a connector 43 is attached to the tube clamp 39. Connector tube 41 is attached to the tube connector 20 on the infusion tube 17 with connector 42, and connector 43 is used to attach connector tube 41 to a source of fluids. The tube clamp 39 or the connector tube 41 decrease the strain on the bone portal 21 by creating the slack in the tube and also prevent the accidental dislodgment of the infusion tube 17 and the bone portal 21 by either clamping the infusion tube 17 or the connector tube 41 to the patch base 47.

Figure 16:
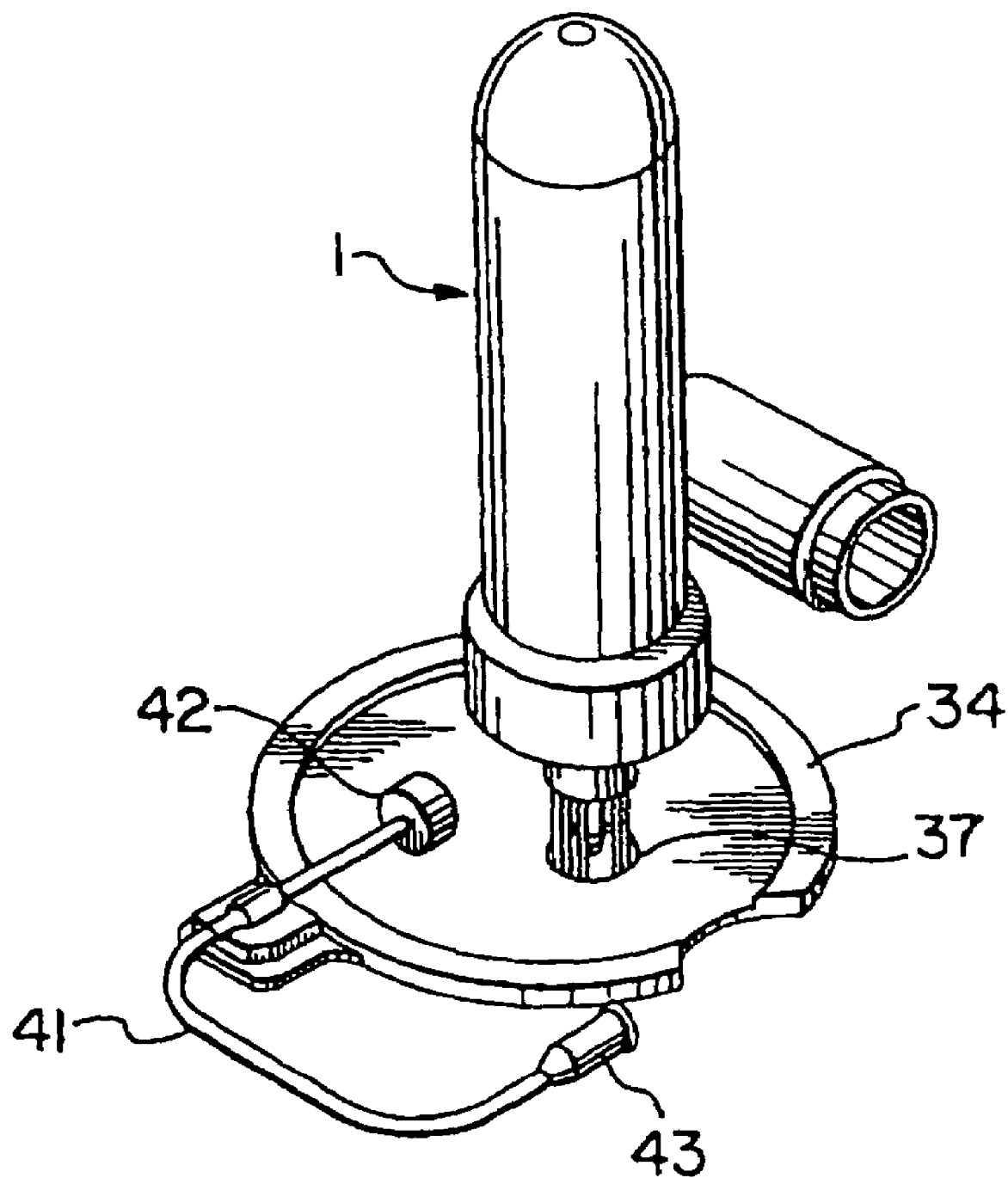
FIG. 16 shows the placement of the intraosseous infusion and aspiration apparatus at the target zone of the template patch.
Figure 17:
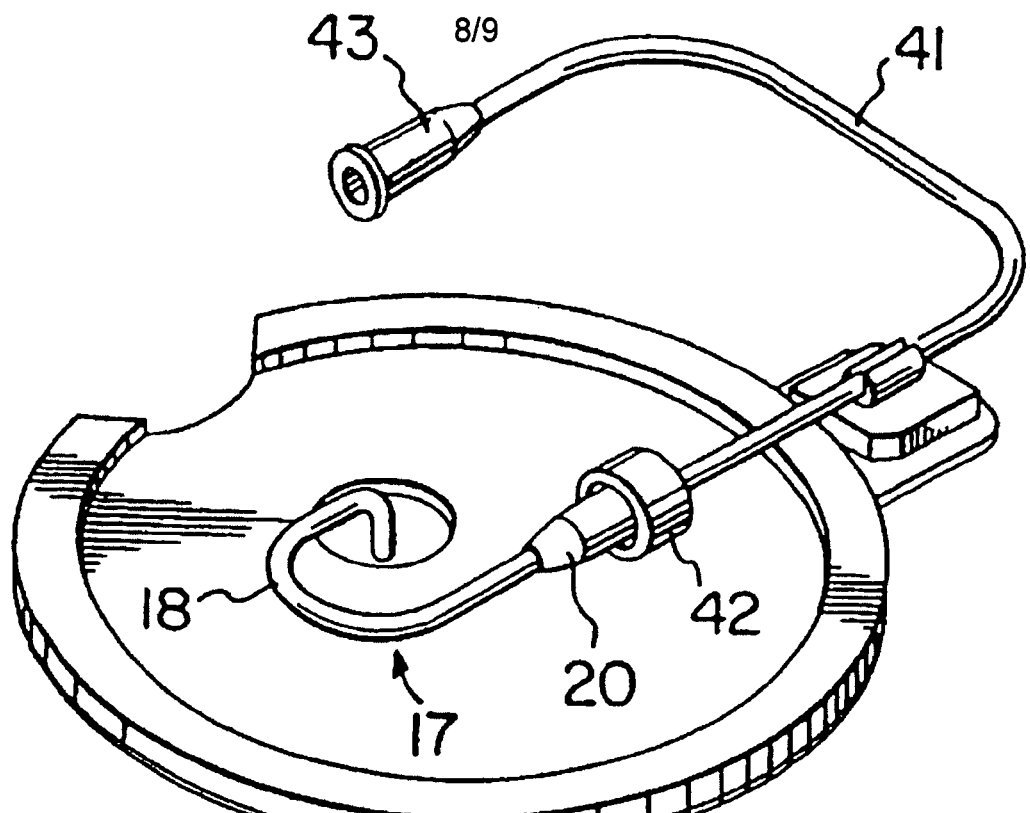
FIG. 17 shows the template patch after the intraosseous infusion and aspiration apparatus has inserted the bone portal into the bone marrow and has been disengaged, and the infusion tube has been connected to the connector tube.

Referring to FIG. 16, the intraosseous infusion and aspiration apparatus 1 is placed perpendicular to the patch 34 in the target zone 37. After the bone portal 21 has been inserted into the bone marrow and the intraosseous infusion and aspiration apparatus 1 removed, the infusion tube 17 is connected to the connector tube 41 with the tube connector 20 and connector 42 as shown in FIG. 17. Connector 43 of the connector tube 41 can be connected to a source of intravenous drugs or fluid.

FIG. 18 shows a preferred embodiment of the cover 44 which has a dome 46 of transparent material with fastening material 45 around its periphery. The dome 46 can be placed on the patch base 47 and the fastening material 38 of the patch base 47 can engage with the fastening material 45 of the cover 44 to protect the site of infusion. The fastening materials can be hook and loop which allows the dome to be removed and reattached.

The intraosseous infusion and aspiration apparatus 1 can be used alone if a patch 34 is not available, or in conjunction with the patch 34. The patch 34 may also be used with other intraosseous infusion and aspiration apparatus. When a patch 34 is used in conjunction with the intraosseous infusion apparatus 1, the top half of the backing of the patch 34 is first removed to expose the adhesive lining on the underside. An appropriate anatomical marker on the appropriate bone is located, for example the sternal notch 36 in the manubrium bone of the patient. An index finger is placed on the anatomical marker perpendicular to the surface of the bone and the peripheral notch 35 on the patch 34 is arranged around the finger in the proper orientation. In this example, the peripheral notch 35 and the target zone 37 are over the patient's midline on the chest. The top half of the patch 34 is pressed onto the skin and the rest of the backing is removed to expose the rest of the adhesive lining that secures the patch 34 to the skin of the patient.

The bone probe needles 31 protective covering 32 is removed, and the bone probe needles 31 are placed on the target zone 37 with the axis of the apparatus 1 perpendicular to the skin of the patient. The hollow outer sleeve 5 is pushed into the target zone 37 until the release of the hollow outer sleeve 5 from the inner sleeve 6 is heard and felt. The hollow outer sleeve 5 is pulled straight back. The support sleeves 33 fall out leaving the infusion tube 17 with bone portal 21 embedded in the patient. A syringe is attached to the infusion tube 17 to withdraw marrow to verify that the infusion tube 17 is at the correct depth in the bone. The bone probe needles 31 protective covering 32 is put back on the apparatus 1 for safety reasons. The infusion tube 17 is connected to a connector tube 41 attached at the patch 34 through the tube connector 20 to provide slack in the tubing and less strain on the infusion site. The connector tube 41 is connected to a supply of intravenous drugs or fluid. The protective cover 44 is placed on the patch 34 so as to engage the covering fastening material 45 with the patch fastening material 38, protecting the infusion tube 17 from dislodgement. After the infusion is complete, the infusion tube 17 may be removed by inserting a remover 23 into the infusion tube 17 and turning it clockwise to engage the threads in the bone portal 21 until the remover stops turning. The remover is then pulled straight out removing the infusion tube 17 from the patient.

Figure 19:
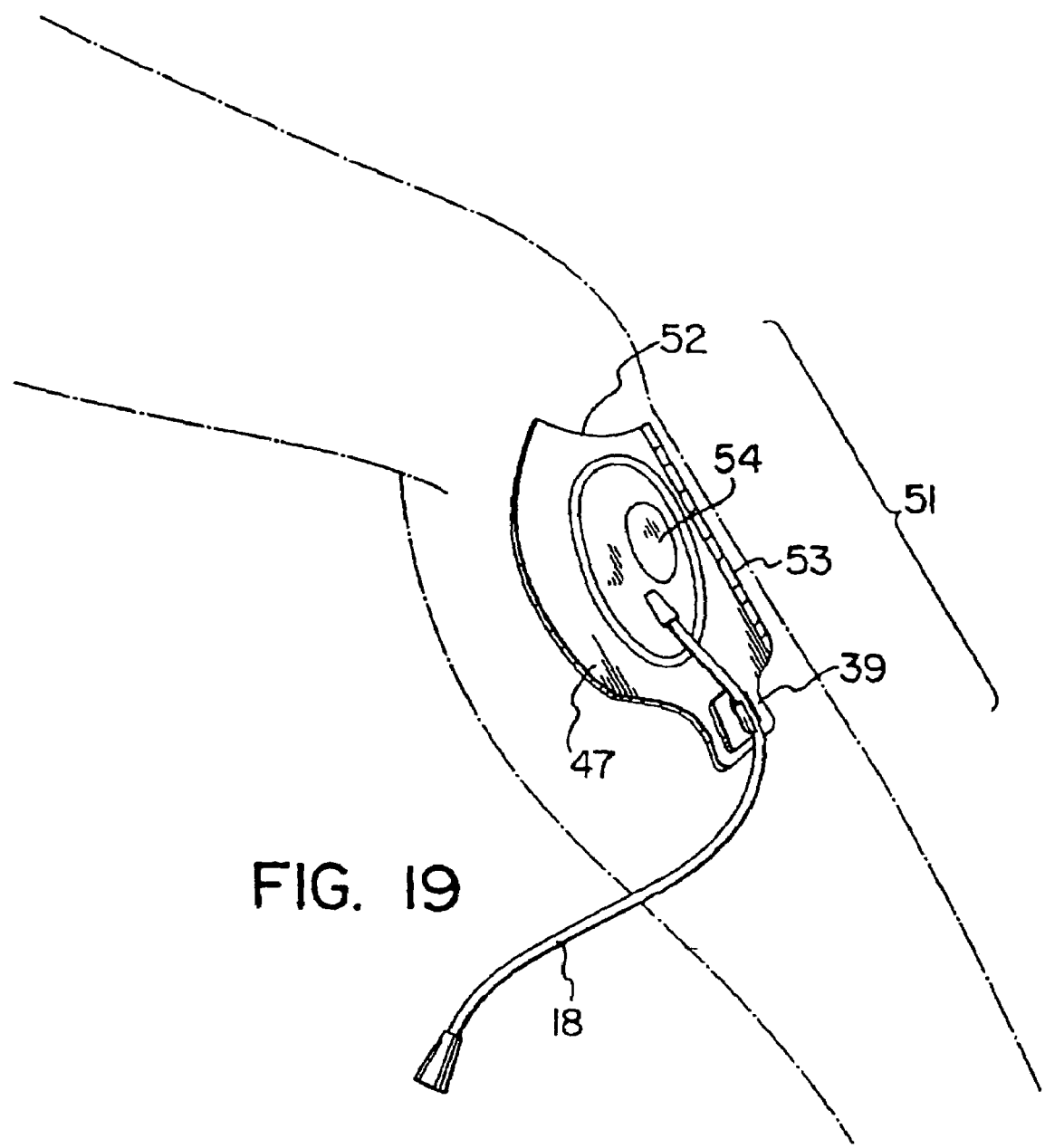
FIG. 19 shows an example of a target patch designed for use at the tibial site for intraosseous infusion.

As an example of the specifications of the apparatus 1 used to infuse the manubrium the following represent a possible design:

Bone probe needles: Ten 1.27 mm hypodermic needles equi-spaced around the bone probe.
angle $\phi=15$ degrees
angle $\theta=60$ degrees
Ball radius=3.16 mm
Maximum force on spring=9.1 kg
Activation distance of bone portal relative to end of bone probe needles=8.87 mm Referring to FIG. 19, a tibial target patch 51 designed for use at the tibial site for intraosseous infusion is shown. This is a site commonly used in children, and occasionally used in adult patients. The tibial site target patch 51 has an alignment feature 52 that is aligned with the tibial tuberosity at the proximal end of the tibia. The tibial target patch 51 has a marking 53 on it for aligning with the ridge of bone that can be felt along the axis of the tibia. The tibial target patch 51 has an adhesive backing with a liner that is removed to place the patch on the skin. The tibial target patch 51 has a tibial target zone 54 that is used as a target for placing any intraosseous needle. This invention removes the need for judging the distances from the anatomical landmarks. The patch could also have an instrument guide (not shown) that guides the needle into the bone at the recommended angle of 45 degrees. The patch could also have loop fasteners for attaching a protective dome designed for placement at this site. The patch could also have a connector tubing bonded to the patch to remove stress and strain from the infusion tube or needle. A similar target patch can easily be envisioned for use at other target sites, for example the distal end of the tibia, near the ankle; the distal end of the femur near the knee; the iliac crest site; or the distal end of the radius (lower arm).

What is claimed is:

1. An adhesive patch for locating a target zone for penetration of a patient's manubrium, said adhesive patch positionable over skin of the patient overlying the manubrium, the adhesive patch comprising:
   a patch base;
   a curved finger-engaging recess formed in the patch base, the finger-engaging recess complementary in size to a sternal notch;
   a target aperture formed in the patch base at a predetermined distance from said curved finger-engaging recess; and
   a tube clamp mounted on said patch base for grippingly engaging a tube to the patch base;
   said curved finger-engaging recess open on one side and at least finger-width, whereby an administrator who is palpating a sternal notch of the patient with a finger can slide the patch toward the finger until the finger-engaging recess engages the palpating finger, thereby positioning said target aperture over the target zone in the patient's manubrium.

2. An adhesive patch according to claim 1, including a strip of fastening material extending around a periphery of said patch base and a covering having fastening material engageable with said strip of fastening material on said patch base and, when so engaged, operative to protect said patch base and at least a portion of said tube from direct contact with external forces.

3. An adhesive patch according to claim 1, wherein said patch base has an extended region outside of said fastening strip and said tube clamp is affixed to said patch base in said extended region.

4. An adhesive patch according to claim 2, wherein said covering comprises a transparent dome.

5. An adhesive patch according to claim 1, comprising a connector tube held by the tube clamp, the connector tube engageable with an infusion tube to prevent stress on said infusion tube caused by external sources.

6. An adhesive patch according to claim 1, wherein the patch base is generally flat.

7. An adhesive patch according to claim 6, wherein the tube clamp is adapted to position at least a portion of a tube being held by the tube clamp in close proximity to the patch base and radially with respect to a center portion of the patch base.

8. An adhesive patch according to claim 1, comprising an infusion tube held by the tube clamp.

9. An adhesive patch according to claim 1, wherein an underside of the patch base is provided with an adhesive.

10. An adhesive patch according to claim 9, comprising a backing on the adhesive, wherein the backing comprises two independently-removable sections, one of the independently-removable sections covering the adhesive in a top portion of the patch which includes the finger-engaging recess.

11. An adhesive patch according to claim 1, wherein the patch base comprises a flexible material.

12. An adhesive patch according to claim 5, wherein the connector tube is flexible.

13. An adhesive patch according to claim 2, wherein the strip of fastening material of the patch base and the fastening material of the covering comprise hook and loop fastening.

14. An adhesive patch for locating a target zone for penetration in a patient, said adhesive patch positionable over the target zone, the adhesive patch comprising:
   a patch base;
   a curved finger-engaging recess formed in an edge of the patch base;
   a target aperture formed in the patch base at a predetermined distance from said curved finger-engaging recess; and
   a tube clamp affixed to said patch base for grippingly engaging a tube to the patch base;
   said curved finger-engaging recess open on one side and at least finger-width, whereby an administrator who is palpating a predetermined landmark on the patient with a finger can slide the patch toward the finger until the finger-engaging recess engages the palpating finger thereby positioning said target aperture over the target zone.

15. An adhesive patch according to claim 14, wherein the patch base is adapted to be received on the patient, wherein the target zone is selected from the group consisting of the manubrium, the tibia, a region of bone proximal to the ankle, a distal end region of the femur proximal to the knee, the iliac crest and a distal end region of the radius.

16. An adhesive patch according to claim 15, wherein the predetermined landmark is the sternal notch and the target zone is the manubrium.

17. An adhesive patch according to claim 15, wherein the predetermined landmark is the tibial tuberosity and the target zone is the tibia.

18. An adhesive patch according to claim 14 further comprising a marking for aligning the adhesive patch with a ridge of bone palpable along the longitudinal axis of the tibia.

19. An adhesive patch for locating a target zone for penetration in a patient, said adhesive patch positionable over the target zone, the adhesive patch comprising:
   a patch base;
   a curved finger-engaging recess formed in an edge of the patch base;
   a strip of fastening material extending around a periphery of said patch base and a covering having fastening material engageable with said strip of fastening material on said patch base;
   a target aperture formed in the patch base at a predetermined distance from said curved finger-engaging recess; and
   a tube fixed on said patch base;
   said curved finger-engaging recess open on one side and at least finger-width, whereby an administrator who is palpating a predetermined landmark on the patient with a finger can slide the patch toward the finger until the finger-engaging recess engages the palpating finger thereby positioning said target aperture over the target zone
   wherein said patch base has an extended region outside of said fastening strip and said tube clamp is affixed to said patch base in said extended region.

20. An adhesive patch according to claim 19, wherein the tube comprises an infusion tube.

21. An adhesive patch according to claim 19, wherein the tube comprises a connector tube engageable with an infusion tube.

22. An adhesive patch according to claim 1, wherein the finger-engaging recess follows an arcuate curve.

23. An adhesive patch according to claim 22, wherein the arcuate curve extends between first and second corners on a periphery of the patch base.

24. An adhesive patch according to claim 3, wherein, relative to the target aperture, the tube clamp is angularly separated from the finger-engaging recess by an acute angle.

* * * * *